United States Patent [19]

Lion et al.

[11] Patent Number: 5,616,598
[45] Date of Patent: Apr. 1, 1997

[54] COSMETIC COMPOSITION COMPRISING A FATTY SUBSTANCE AND AN AQUEOUS POLYMER DISPERSION AND THE USE THEREOF

[75] Inventors: Bertrand Lion, Livry Gargan; Jean Mondet, Aulnay Sous Bois, both of France

[73] Assignee: L'Oreal, Paris, France

[21] Appl. No.: 478,024

[22] Filed: Jun. 7, 1995

[30] Foreign Application Priority Data

Jun. 17, 1994 [FR] France .................................. 94 07480

[51] Int. Cl.$^6$ .......................... A01N 43/76; A61K 31/74; A61K 7/32
[52] U.S. Cl. .......................... 514/374; 424/63; 424/64; 424/69; 424/78.02; 424/78.03; 514/844; 514/846; 514/847; 514/848
[58] Field of Search ...................... 514/844, 848, 514/846, 847; 424/69, 64, 63, 78.02, 78.03

[56] References Cited

U.S. PATENT DOCUMENTS

| | | | |
|---|---|---|---|
| 4,198,330 | 4/1980 | Kaizerman et al. | 525/185 |
| 4,300,580 | 11/1981 | O'Neill et al. | 132/7 |
| 4,946,932 | 8/1990 | Jenkins | 528/272 |
| 5,254,542 | 10/1993 | Sakuta et al. | 514/63 |

FOREIGN PATENT DOCUMENTS

| | | |
|---|---|---|
| 0297576 | 1/1989 | European Pat. Off. . |
| 0309114 | 3/1989 | European Pat. Off. . |
| 0353896 | 2/1990 | European Pat. Off. . |
| 0478284 | 4/1992 | European Pat. Off. . |
| 2680684 | 3/1993 | France . |
| 2238242 | 5/1991 | United Kingdom . |

OTHER PUBLICATIONS

Research Disclosure, "Hair Grooming Compositions", vol. 326, (1991) New York (USA), pp. 390–391.
Research Disclosure, "Fast Drying Aqueous Nail Polish", vol. 326, (1991) New York (USA), p. 395.

*Primary Examiner*—Terressa Mosley
*Attorney, Agent, or Firm*—Finnegan, Henderson, Farabow, Garrett & Dunner, L.L.P.

[57] ABSTRACT

The present application relates to a cosmetic composition, in particular a care or make-up composition to be applied to the skin and/or to the eyelashes, which comprises at least one fatty substance and at least one aqueous polymer dispersion consisting of particles resulting from the polymerization of a radical monomer in the interior and/or partially at the surface of already existing polymer particles of polyester type.

33 Claims, No Drawings

COSMETIC COMPOSITION COMPRISING A FATTY SUBSTANCE AND AN AQUEOUS POLYMER DISPERSION AND THE USE THEREOF

The present application relates to a cosmetic composition, in particular a care or make-up composition, which comprises at least one fatty substance and at least one aqueous polymer dispersion consisting of particles resulting from the polymerization of a radical monomer in the interior and/or partially at the surface of already existing polymer particles of polyester type.

The invention also relates to the use of such a dispersion, in particular as a film-forming agent, in a cosmetic composition.

It is known to use aqueous polymer dispersions as film-forming agent in make-up compositions comprising fatty substances, for example in mascaras. The properties of the aqueous dispersions thus obtained, and therefore of the final cosmetic compositions, depend on the nature of the polymers, and therefore of the monomers, from which they are prepared. However, it may be an advantage to be able to modify slightly these properties, for example by accentuating/optimizing a particularly advantageous property, or by developing a new property which the said dispersion could not have on the basis of its inherent composition.

An object of the invention is to provide a cosmetic composition comprising a fatty substance and an aqueous dispersion of a polymer chosen from the group consisting of polyesters, polyesteramides and alkyds, the said dispersion, and thus the said composition, having properties which are improved relative to the polyester, polyesteramide and/or alkyd dispersions of the prior art.

Another object of the invention is therefore a cosmetic composition comprising at least one fatty substance and an aqueous polymer dispersion consisting of particles resulting from the free-radical polymerization of at least one radical monomer in the interior and/or partially at the surface of already existing particles of at least one polymer chosen from the group consisting of polyesters, polyesteramides and alkyds.

Still another object of the invention is the use of an aqueous polymer dispersion consisting of particles resulting from the free-radical polymerization of at least one radical monomer in the interior and/or partly at the surface of already existing particles of at least one polymer chosen from the group consisting of polyesters, polyesteramides and alkyds as film-forming agent in such a composition, or else in order to improve the remanence properties with respect to water or the removal properties of the said composition as make-up. In particular, when the composition is present in the form of a mascara or eyeliner, the use of a dispersion according to the invention makes it possible to improve the eyelash elongation properties, remanence properties with respect to water and/or removal properties of the composition as make-up.

In the rest of the present description, "polyester" is intended to mean any polymer, individually or as a mixture, chosen from the group consisting of polyesters, polyesteramides and alkyds.

It has been found that the use of aqueous dispersions according to the invention, i.e. of aqueous dispersions of hybrid polyester polymers, makes it possible to obtain a cosmetic composition which has properties, for example remanence with respect to water, make-up removal or else film-forming properties, which are improved, such properties being impossible to obtain by using, for example, a simple mixture of existing aqueous dispersions of polyester and of acrylic and/or vinyl polymer. An advantage of the present invention is therefore to be able, on the basis of an already existing aqueous polymer dispersion, to develop and/or optimize certain particularly advantageous properties in a relatively controlled manner. Thus, taking as example a mascara for application to the eyelashes, it is possible—depending on the nature of the polymers and monomers used to form the dispersion—to obtain a mascara whose remanence with respect to water is improved, or conversely whose removal as make-up is made easier, or else to obtain a mascara which has a notable capacity for elongation of the eyelash.

In preparing the composition according to the invention, an aqueous polyester dispersion is prepared first of all. This dispersion may be prepared by the person skilled in the an on the basis of their general technical knowledge, in particular as follows. When the polyester polymer is insoluble in water, it is possible to dissolve it in an organic solvent which is slightly soluble in water, to add water so as to form an emulsion, and then to evaporate the organic solvent so as to obtain an aqueous dispersion of the polyester polymer in water, having a solids content of approximately 30–50% by weight. When the polyester polymer is autodispersible in water, this step may be omitted if the polymer has a sufficient content of hydrophilic groups.

The aqueous "polyester" dispersion used may be an aqueous dispersion of an anionic, cationic, non-ionic or amphoteric polyester, of polyesteramides, or of alkyds, i.e. of fatty-chain polyesters, individually or as a mixture. The dispersion may also be a dispersion of polyesters containing ionizable side groups, such as sulpho or carboxyl groups. The polyester may contain unsaturated groups, for example when it is obtained by polycondensation of a diol or a diamine with an unsaturated acid anhydride, for example maleic anhydride. The charge of the radical monomer may in this case subsequently react with the unsaturated polyester and give rise to grafting and/or to crosslinking. In this way a dispersion of a grafted and/or crosslinked hybrid polymer is obtained which may impart to the film obtained after application of the dispersion particular mechanical properties, such as an improvement in the adhesion of the said film.

The aqueous dispersion of hybrid polyester polymers according to the invention is obtained by free-radical polymerization of at least one monomer in the interior and/or partially at the surface of already existing polyester particles. The radical monomer may be vinyl or acrylic in nature and may be anionic, cationic, non-ionic or amphoteric. It is also possible to use a mixture of monomers of different kinds. The monomer or monomer mixture is preferably insoluble or slightly soluble in water. Monomers which can be employed include the esters of acrylic or methacrylic acid, such as methyl, ethyl, propyl, butyl, isobutyl, tert-butyl and 2-ethylhexyl acrylate or methacrylate; N-substituted or N,N-substituted acrylamides or methacrylamides; vinyl esters such as vinyl acetate; and styrene. It is also possible to use, individually or as a mixture, a vinyl, acrylic or methacrylic monomer which contains one or more siloxane groups, in particular:

the monomer of formula

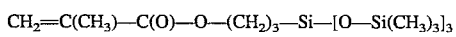

a silicon-containing macromonomer with a monofunctional vinyl, allyl, methacrylic or acrylic acid ester, ether or amide end group, of formula

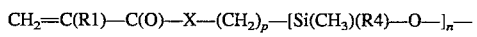

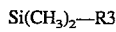

in which R1 represents H or CH$_3$, X represents O or NH, p is an integer which may be zero, R3 and R4 independently represent CH$_3$ or an aliphatic, cycloaliphatic or aromatic group, and n is an integer which is preferably between 3 and 300. It is also possible to use a vinyl or allyl monomer or a methacrylic or acrylic acid ester, ether or amide monomer which contains one or more halogenated groups, especially chlorinated and/or fluorinated groups, and/or which contains a group which absorbs in UV and which may, after polymerization, provide a certain photoprotection against UV radiation, especially solar radiation, for example substituted or unsubstituted benzylidenecamphor and/or benzotriazole groups such as 2-(2'-hydroxy-5-methacryloyloxyethylphenyl)-2H-benzotriazole.

When the monomer or monomer mixture is in liquid form at room temperature, the free-radical polymerization may be carried out without employing a solvent. When the monomer or monomer mixture is in solid form at room temperature, it may be dissolved prior to polymerization, preferably in an organic solvent, for example a polar and water-miscible solvent such as methanol. In this case, after polymerization, it is possible to distil off the organic solvent present in the aqueous dispersion, if necessary.

The aqueous dispersions according to the invention are prepared under conditions such that the monomer polymerizes in the interior and/or partially at the surface of the polymer particles without any nucleation, i.e. without the formation of new particles. In order to achieve this, it is possible to introduce the polyester polymer, in an aqueous dispersion having a solid content of 30–50% by weight, into a polymerization reactor. It is then possible to add to this reactor the monomer or the monomer mixture, as it is or in solution in an appropriate solvent, and a free-radical polymerization initiator. Depending on what kind it is, the free-radical initiator is introduced in the form of a solution in an organic solvent, in the form of an aqueous solution, or else dissolved beforehand in the monomer mixture. In the first case, it may be added at the same time as the monomer in solution, and in the second case it may be added after the monomer. It is possible to use an organic free-radical polymerization initiator which is not soluble in water, of the peroxide or percarbonate type, such as tert-butylperoxy-2-ethylhexanoate, or an organic initiator which is soluble in water, or else an inorganic initiator such as potassium persulphate. An aqueous mixture is thus prepared which comprises the polyester polymer, the monomer and the polymerization initiator. It is also possible to add to this mixture a stabilizer which may be, in particular, a surfactant or a mixture of surfactants which is or are anionic, amphoteric, cationic and/or non-ionic. When the polyester used is itself ionic, it is preferable to use a surfactant of the same, ionic or amphoteric type. It is preferred to use an ionic and polyoxyethylenated surfactant in a quantity of 0.5–10% by weight of solids relative to the weight of polyester solids. This mixture is heated to the required temperature so as to allow the decomposition of the initiator, and polymerization is continued until the monomers have been consumed.

The proportions of radical monomer to polyester polymer may be 10–95% by weight of radical monomer solids and 5–90% by weight of polyester solids.

An aqueous dispersion of hybrid polymer is thus obtained whose constituent particles are present in the form of composite particles, similar to an "alloy" of the two base polymers, and whose size is comparable to that of the polyester particles prior to free-radical polymerization. The dispersions thus obtained possess characteristic properties which are different from those which would be obtained by mixing two aqueous dispersions of each of the constituents.

The dispersions according to the invention may be used in skin-care compositions such as creams, lotions, gels or solutions, or in make-up compositions such as lipsticks, foundations, blushers or eyeshadows, mascaras or eyeliners. It is also possible to use the dispersions according to the invention in products which are intended for the photoprotection of the skin and/or of keratinous material against UV radiation, in particular against solar radiation, when they contain an appropriate monomer which is able to provide a certain sun protection. These compositions comprise the ingredients which are conventionally employed in the field under consideration, and may be prepared according to the usual methods which are known to the person skilled in the art. In particular, these compositions comprise at least one fatty substance which may be chosen from conventional fatty substances such as hydrocarbon-and/or silicon-containing waxes and/or oils, which may be volatile.

It is thus possible to employ any wax which is known in the prior art, and in particular inorganic waxes such as microcrystalline waxes, paraffin, petrolatum, petroleum jelly, ozocerite, montan wax; animal waxes such as beeswax, lanolin and derivatives thereof; vegetable waxes such as candelilla wax, ouricury wax, carnauba wax, Japan wax, cocoa butter, cork fibre wax or sugar-cane wax; hydrogenated oils, fatty esters and glycerides which are solid at 25° C.; synthetic waxes such as polyethylene waxes and waxes obtained by Fischer-Tropsch synthesis; and silicone waxes. It is also possible to employ an oil or a mixture of oils which are conventionally employed in cosmetics, among which there may be mentioned mineral oils such as paraffin oil or liquid paraffin; animal oils such as perhydrosqualene or arara oil; vegetable oils such as sweet almond oil, calophyllum oil, palm oil, castor oil, avocado oil, jojoba oil, olive oil or cereal germ oil; silicone oils; esters of lanolin acid, oleic acid, lauric acid, stearic acid or myristic acid, for example; alcohols such as oleyl alcohol, linoleyl alcohol or linolenyl alcohol, isostearyl alcohol or octyl dodecanol; acetyl glycerides, octanoates, decanoates or ricinoleates of alcohols or of polyalcohols. These oils may also be at least partially volatile.

The composition may additionally comprise pigments and/or nacreous substances and/or fillers which are conventionally employed in cosmetics. The pigments may be white or coloured, inorganic and/or organic. The inorganic pigments include titanium dioxide, zirconium dioxide or cerium dioxide, and oxides of zinc, or iron or of chromium, and iron blue.

The organic pigments include carbon black and the lakes of barium, strontium, calcium and aluminium. Among the nacreous substances, it is possible to mention mica covered with titanium oxide or with iron oxide, natural pigment or bismuth oxychloride, and also coloured titanium mica. The fillers may be inorganic or synthetic, lamellar or non-lamellar. Mention may be made of talc, mica, silica, kaolin, nylon powder, polyethylene powder, Teflon, starch, titanium mica, natural mother of pearl, boron nitride, microspheres such as Expancel (Nobel Industrie), polytrap (Dow Coming) and silicone resin microballs.

The composition may additionally comprise any additive which is conventionally employed in the cosmetics field, such as antioxidants, fragrances, essential oils, preservatives, cosmetic active substances, moisturizers, vitamins, essential fatty acids, sphingoceryls, sunscreens, surfactants, lipid-soluble polymers such as polyalkenes, especially polybutene, polyacrylates and silicon-containing polymers which are compatible with the fatty substances. The person skilled in the art will of course ensure that any additional compound, and/or their quantity, are chosen such that the advantageous properties of the composition according to the invention are not or are not substantially altered by the addition envisaged.

The invention is illustrated in greater detail in the examples which follow, in which percentages are given by weight.

EXAMPLE 1

50 g of solid granules of a polyester polymer containing sulpho groups (AQ 38 sold by Eastman Kodak), were dispersed in 250 ml of deionized water heated beforehand to 80° C., while maintaining shear stirring with the aid of a Moritz type disperser. A dispersion was obtained which had a mean particle size of 40 nm with a polydispersity of 0.15. The dispersion was left to stand for 24 hours and was then introduced into a reactor which had been heated beforehand to 80° C.; 50 g of methyl methacrylate were added dropwise, which took about 45 minutes, and the mixture was then stirred for 1 hour at 80° C. 0.5 ml of tert-butylperoxy-2-ethylhexanoate (Trigonox 21S from Akzo) were added and the mixture was left to react for 6 hours with stirring and bubbling in of nitrogen at 80° C.

The mixture which was then obtained had the same appearance as at the beginning, even though all of the monomer had polymerized. The temperature of the reaction mixture was reduced to 25° C., the mixture was filtered through a nylon cloth, and the dispersion was concentrated under reduced pressure until a solids content of 40% was obtained. A dispersion was thus obtained which, after a further filtration, had the following characteristics:

mean particle size, determined by a Coulter N4 quasi-elastic light diffusion apparatus from Coultronix: 44 nm polydispersity: 0.15

Taking into account that the size of the particles in the initial dispersion of polyester AQ 38 was 40 nm (polydispersity: 0.15), it may thus be noted that the polymerization of the monomer produced virtually no change in the size of the said initial particles.

The absence of double distribution in particles signifies that polymerization did not lead to the creation of a second population of particles in addition to the initial population.

The dispersion obtained was an aqueous dispersion of a hybrid polymer whose particles resulted from the free-radical polymerization of a methyl methacrylate monomer on and/or in the particles of an already existing polymer of the polyester type containing sulpho groups.

EXAMPLES 2 to 5

In a manner similar to that described in Example 1, an aqueous dispersion of granules of sulpho polyester, AQ 38 from Eastman Kodak, was used to prepare various hybrid polymers according to the table below. Initiation was carried out in each case with 0.5 ml of Trigonox 21S. The measurements of particle size and of polydispersity were carried out for a dispersion having a solids content of 40%.

|  | polyester | water added | monomer | particle size | poly-dispersity |
|---|---|---|---|---|---|
| Example 2 | 70 g | 250 ml | 30 g of methyl methacrylate | 35 nm | 0.10 |
| Example 3 | 50 g | 250 ml | 45 g of methyl methacrylate + 5 g of ethylene glycol dimethacrylate | 45 nm | <0.10 |
| Example 4 | 70 g | 250 ml | 30 g of isobutyl methacrylate | 45 nm | 0.12 |
| Example 5 | 70 g | 300 ml | 25 g of methyl methacrylate + 5 g of ethylene glycol dimethacrylate | 32 nm | 0.18 |

It was observed that for all these examples a unique and homogeneous population of particles was obtained whose size underwent little modification by the polymerization.

EXAMPLE 6

The film-forming properties of the dispersions of the polymers according to the invention were compared at room temperature. It was observed that the dispersions of examples 1, 2, 3 and 5 formed films when a plasticizer (20 g of tripropylene glycol monomethyl ether per 100 g of dispersion solids) was added to them, and made it possible to obtain films which are homogeneous and transparent after drying.

EXAMPLE 7

40 g of solid granules of a polyester polymer containing sulpho groups, AQ 38 sold by Eastman Kodak, were dispersed in 160 ml of deionized water heated beforehand to 80° C., while maintaining shear stirring with the aid of a Moritz type disperser. The dispersion was left to stand for 24 hours and then introduced into a reactor heated beforehand to 80° C.; 15.8 g of an aqueous solution of Octaron PS20 (polyoxyethylenated nonylphenol (4.5 EO) sulphated at the chain end), sold by Seppic at a concentration of 20.25% solids, were added. After stirring, 0.4 ml of tert-butylperoxy-2-ethylhexanoate (Trigonox 21S from Akzo) was introduced and the mixture was brought to 80° C. with stirring and bubbling in of nitrogen. 10 g of butyl acrylate were added and the mixture was left to react for 8 hours. The temperature of the reaction mixture was reduced to 25° C., the mixture was filtered through a nylon cloth, and the dispersion was concentrated under reduced pressure until a solids content of 33% was obtained. A dispersion was thus obtained which had the following characteristics:

mean particle size, determined by a Coulter N4 quasi-elastic light diffusion apparatus from Coultronix: 25 nm polydispersity: 0.4

EXAMPLE 8

An aqueous dispersion of 2.5 grams of polyester polymer containing sulpho groups, AQ 38 sold by Eastman Kodak, was prepared in 200 ml of deionized water and introduced into a reactor heated beforehand to 80° C. 2.5 grams of sodium lauryl sulfate were added, followed by addition of 0.25 grams of potassium persulfate and 0.25 grams of sodium hydrogencarbonate.

The mixture was heated to 72° C., and then a mixture of 42.75 grams of tertbuylyacrylate was added together with 4.75 grams of silicon macromonomer sold by 3M (molecular weight 9,000 to 12,000).

The mixture was maintained at 72° C. under stirring for 24 hours; then the temperature of the reaction mixture was lowered to 25° C. The mixture was then filtered by means of a nylon cloth, and the dispersion, under reduced pressure, was then concentrated to obtain a ratio of 20% solids content.

The dispersion obtained was an aqueous dispersion of a hybrid polymer wherein silicone macromonomer and tert-butylacrylate monomers were polymerized within and/or partially at the surface of the preexisting particles of polymer of the polyester polymer containing sulpho groups.

EXAMPLE 9

An aqueous dispersion of 2.5 grams of polyester polymer containing sulpho groups, AQ 38 sold by Eastman Kodak, was prepared in 200 ml of deionized water and introduced into a reactor heated beforehand to 80° C. 2.5 grams of sodium lauryl sulfate were added, followed by addition of 0.25 grams of potassium persulfate and 0.25 grams of sodium hydrogencarbonate.

The mixture was heated to 72° C., and then a mixture of 42.75 grams of tertbuylyacrylate was added together with 4.75 grams of perfluorohexyl acrylate (ATOCHEM).

The mixture was maintained at 72° C. under stirring for 24 hours; then the temperature of the reaction mixture was lowered to 25° C. The mixture was then filtered by means of a nylon cloth, and the dispersion, under reduced pressure, was then concentrated to obtain a ratio of 20% solids content.

The dispersion obtained was an aqueous dispersion of a hybrid polymer wherein perfluorohexyl acrylate and tertbutylacrylate monomers were polymerized within and/or partially at the surface of the preexisting particles of polymer of the polyester polymer containing sulpho groups.

EXAMPLE 10

A mascara composition was prepared as follows. 11.5 g of triethanolamine stearate, 7.0 g of beeswax, 4.1 g of carnauba wax and 11.4 g of paraffin were mixed. The mixture was brought to 85° C., and 5.5 g of black iron oxide were added. A second mixture was prepared comprising 35 ml of water, 4.5 g of gum arabic and 0.16 g of hydroxyethylcellulose, and this mixture was heated to 85° C. The two mixtures were combined, and 21.3 g of one of the dispersions of the preceding examples were added, diluted or concentrated so as to have a solids content of 25% by weight. A mascara was obtained which had good cosmetic characteristics for application to the eyelashes, with consistent elongation, and good remanence with respect to water.

What is claimed is:

1. A cosmetic composition, which comprises at least one fatty substance and an aqueous polymeric dispersion comprising particles composed of at least one radical monomer and at least one polymer chosen from polyesters, polyesteramides, and alkyds, said at least one radical monomer being polymerized within and/or partially at the surface of the particles of said at least one polymer.

2. The composition of claim 1, wherein said at least one radical monomer is an ester of acrylic or methacrylic acid; an N-substituted or N,N-substituted acrylamide or methacrylamide; a vinyl ester; styrene; a vinyl, acrylic or methacrylic monomer comprising one or more siloxane groups; a vinyl or allyl monomer or an acrylic or methacrylic acid ester, ether or amide monomer containing at least one group selected from halogenated groups and a group capable of absorbing in at least one region selected from UVA and UVB and being able to provide, after polymerization, photoprotection against ultraviolet radiation.

3. The composition of claim 2, wherein the halogenated groups are selected from chlorinated and fluorinated groups.

4. The composition of claim 2, wherein the group capable of absorbing in at least one region is a substituted or unsubstituted group selected from benzylidenecamphor and benzotriazole.

5. The composition of claim 4, wherein the benzotriazole group is 2-(2'-hydroxy-5-methacryloyloxyethylphenyl)-2H-benzotriazole.

6. The composition of claim 2, wherein the siloxane group is:

a monomer of formula $CH_2=C(CH_3)-C(O)-O-(CH_2)_3-Si-_3$ or a silicon-containing macromonomer with a monofunctional vinyl, allyl, methacrylic or acrylic acid ester, ether or amide end group of formula $CH_2=C(R1)-C(O)-X-(CH_2)_p-[Si(CH_3)(R4)-O-]_n-Si(CH_3)_2-R3$, in which R1 represents H or $CH_3$, X represents O or NH, p is an integer which is optionally zero, R3 and R4 independently represent an aliphatic, cycloaliphatic or aromatic group, and n is an integer.

7. The composition of claim 6, wherein n is an integer of 3 to 300.

8. The composition of claim 1, wherein the polymer of said preexisting particles is an anionic, cationic, non-ionic or amphoteric polyester, polyether with ionizable side groups, or polyester containing unsaturated side groups.

9. The composition of claim 8, wherein the ionizable side groups are selected from sulpho and carboxyl groups.

10. The composition of claim 1, wherein the radical monomer is present in an amount ranging from about 10–95% by weight, and the polymer of said preexisting particles is present in an amount ranging from about 5–90% by weight.

11. A skin-care composition comprising an effective amount of the composition of claim 1 in said skin-care composition.

12. A composition for the photoprotection of skin and/or of keratinous material against UV radiation, which comprises an effective amount of the composition of claim 1 in said photoprotection composition.

13. A method of forming a film in a cosmetic composition, comprising the step of forming said film with an effective amount of a fatty substance and an aqueous polymeric dispersion comprising of particles composed of at least one radical monomer free-radically polymerized within and/or partially at the surface of preexisting particles of at least one polymer chosen from polyesters, polyesteramides, and alkyds.

14. A method of improving the remanence properties with respect to water or the removal properties of a make-up composition comprising the step of including in said makeup composition for the purpose of improving said remanence properties or improving said removal properties an effective amount of the cosmetic composition of claim 1.

15. A method of improving the eyelash elongation properties, or the remanence with respect to water, or the removal properties of an eyeliner and/or mascara composition comprising the step of including in said composition for the purpose or improving said eyelash elongation properties or said remanence or removal properties an effective amount of the cosmetic composition of claim 1.

16. The method of claim 13, wherein said at least one radical monomer is an ester of acrylic or methacrylic acid; an N-substituted or N,N-substituted acrylamide or methacrylamide; a vinyl ester; styrene; a vinyl, acrylic or methacrylic monomer comprising one or more siloxane groups; a vinyl or allyl monomer or an acrylic or methacrylic acid ester, ether or amide monomer containing at least one group selected from halogenated groups and a group capable of absorbing UV and being able to provide, after polymerization, photoprotection against ultraviolet radiation.

17. The method of claim 14, wherein said at least one radical monomer is an ester of acrylic or methacrylic acid; an N-substituted or N,N-substituted acrylamide or methacrylamide; a vinyl ester; styrene; a vinyl, acrylic or methacrylic monomer comprising one or more siloxane groups; a vinyl or allyl monomer or an acrylic or methacrylic acid ester, ether or amide monomer containing at least one group selected from halogenated groups and a group capable of absorbing UV and being able to provide, after polymerization, photoprotection against ultraviolet radiation.

18. The method of claim 15, wherein said at least one radical monomer is an ester of acrylic or methacrylic acid; an N-substituted or N,N-substituted acrylamide or methacrylamide; a vinyl ester; styrene; a vinyl, acrylic or methacrylic monomer comprising one or more siloxane groups; a vinyl or allyl monomer or an acrylic or methacrylic acid ester, ether or amide monomer containing at least one group selected from halogenated groups and a group capable of absorbing in at least one region selected from UVA and UVB and being able to provide, after polymerization, photoprotection against ultraviolet radiation.

19. The method of claim 16, wherein the halogenated groups are selected from chlorinated and fluorinated groups.

20. The method of claim 19, wherein the group capable of absorbing in said at least one region UV is a substituted or unsubstituted group selected from benzylidenecamphor and benzotriazole.

21. The method of claim 20, wherein the benzotriazole group is 2-(2'-hydroxy-5-methacryloyloxyethylphenyl)-2H-benzotriazole.

22. The method of claim 16, wherein the siloxane group is:

a monomer of formula $CH_2=C(CH_3)-C(O)-O-(CH_2)_3-Si[O-Si(CH_3)_3]_3$ or a silicon-containing macromonomer with a monofunctional vinyl, allyl, methacrylic or acrylic acid ester, ether or amide end group of formula $CH_2=C(R1)-C(O)-X-(CH_2)_p-[Si(CH_3)(R4)-O-]_n-Si(CH_3)_2-R3$, in which R1 represents H or $CH_3$, X represents O or NH, p is an integer which is optionally zero, R3 and R4 independently represent an aliphatic, cycloaliphatic or aromatic group, and n is an integer.

23. The method of claim 22, wherein n is an integer of 3 to 300.

24. The method of claim 13, wherein the polymer of said preexisting particles is an anionic, cationic, non-ionic or amphoteric polyester, polyether with ionizable side groups, or polyester containing unsaturated side groups.

25. The composition of claim 24, wherein the ionizable side groups are selected from sulpho and carboxyl groups.

26. The method of claim 13, wherein the radical monomer is present in an amount ranging from about 10–95% by weight, and the polymer of said preexisting particles is present in an amount ranging from about 5–90% by weight.

27. The method of claim 13, wherein said cosmetic composition is a skin-care composition.

28. The method of claim 13, wherein said cosmetic composition is selected from a lipstick, a foundation, a blusher, eyeshadow, a mascara, and an eyeliner.

29. The method of claim 13, wherein said cosmetic composition is a photoprotection composition for the protection of skin and/or of keratinous material against radiation in at least one region selected from UVA and UVB.

30. The composition of claim 6, wherein said aliphatic group of $R_3$ and $R_4$ is $CH_3$.

31. The method of claim 22, wherein said aliphatic group of $R_3$ and $R_4$ is $CH_3$.

32. A lipstick, foundation, blusher, eyeshadow, mascara, or eyeliner composition, which comprises an effective amount of the composition of claim 1.

33. A cosmetic composition of claim 1, wherein said at least one radical monomer is crosslinked or grafted within and/or partially at the surface the particles of said at least one polymer.

* * * * *